US007439351B2

(12) United States Patent
Gosselin et al.

(10) Patent No.: US 7,439,351 B2
(45) Date of Patent: Oct. 21, 2008

(54) 2' OR 3'-DEOXY AND 2', 3'-DIDEOXY-β-L-PENTOFURANONUCLEO-SIDE COMPOUNDS, METHOD OF PREPARATION AND APPLICATION IN THERAPY, ESPECIALLY AS ANTI-VIRAL AGENTS

(75) Inventors: Gilles Gosselin, Montpellier (FR); Jean-Louis Imbach, Montpellier (FR); Anne-Marie Aubertin, Strasbourg (FR); Jean-Pierre Sommmadossi, Cambridge, MA (US); Raymond F. Schinazi, Decatur, GA (US)

(73) Assignees: The UAB Research Foundation, Birmingham, AL (US); Emory University, Atlanta, GA (US); Centre National de la Recherche Scientifique (CNSR), Paris (FR)

( * ) Notice: Subject to any disclaimer, the term of this patent is extended or adjusted under 35 U.S.C. 154(b) by 254 days.

(21) Appl. No.: 10/672,585

(22) Filed: Sep. 26, 2003

(65) Prior Publication Data
US 2005/0101776 A1 May 12, 2005

Related U.S. Application Data

(63) Continuation of application No. 09/953,187, filed on Sep. 14, 2001, now abandoned, which is a continuation of application No. 08/612,965, filed on Jul. 29, 1997, now abandoned.

(30) Foreign Application Priority Data

Sep. 10, 1993 (FR) .................................. 93 10798
Sep. 9, 1999 (WO) ...................... PCT/FR94/01066

(51) Int. Cl.
C07H 19/073 (2006.01)
C07H 19/173 (2006.01)
(52) U.S. Cl. ................. 536/27.11; 536/27.14; 536/27.1
(58) Field of Classification Search ............. 536/27.11, 536/27.14, 27.1
See application file for complete search history.

(56) References Cited

U.S. PATENT DOCUMENTS

| 3,116,282 A | 12/1963 | Hunter et al. |
|---|---|---|
| 3,553,192 A | 1/1971 | Gauri et al. |
| 4,000,137 A | 12/1976 | Dvonoch et al. |
| 4,140,761 A | 2/1979 | Gerin et al. |
| 4,336,381 A | 6/1982 | Nagata et al. |
| 4,818,538 A | 4/1989 | Rideout et al. |
| 4,861,759 A | 8/1989 | Mitsuya et al. |
| 4,879,277 A | 11/1989 | Mitsuya et al. |
| 4,900,828 A | 2/1990 | Belica et al. |
| 4,916,122 A | 4/1990 | Chu et al. |
| 4,963,533 A | 10/1990 | de Clercq et al. |
| 5,041,449 A | 8/1991 | Belleau et al. |
| 5,047,407 A | 9/1991 | Belleau et al. |
| 5,059,690 A | 10/1991 | Zahler et al. |
| 5,089,500 A | 2/1992 | Daluge |
| 5,149,794 A | 9/1992 | Yatvin et al. |
| 5,151,426 A | 9/1992 | Belleau et al. |
| 5,179,104 A | 1/1993 | Chu et al. |
| 5,185,437 A | 2/1993 | Koszalka et al. |
| 5,194,654 A | 3/1993 | Hostetler et al. |
| 5,204,466 A | 4/1993 | Liotta et al. |
| 5,210,085 A | 5/1993 | Liotta et al. |
| 5,223,263 A | 6/1993 | Hostetler et al. |
| 5,234,913 A | 8/1993 | Furman, Jr. |
| 5,248,776 A | 9/1993 | Chu et al. |
| 5,256,641 A | 10/1993 | Yatvin et al. |
| 5,270,315 A | 12/1993 | Belleau et al. |
| 5,276,151 A | 1/1994 | Liotta |
| 5,411,947 A | 5/1995 | Hostetler et al. |
| 5,444,063 A | 8/1995 | Schinazi |
| 5,463,092 A | 10/1995 | Hostetler et al. |
| 5,466,806 A | 11/1995 | Belleau et al. |
| 5,486,520 A | 1/1996 | Belleau et al. |
| 5,532,246 A | 7/1996 | Belleau et al. |
| 5,539,116 A | 7/1996 | Liotta et al. |
| 5,543,389 A | 8/1996 | Yatvin et al. |

(Continued)

FOREIGN PATENT DOCUMENTS

EP    0 217 580 A2    4/1987

(Continued)

OTHER PUBLICATIONS (R) Périgaud et al., "Potential Antiviral Agents. Sterospecific Synthesis of Purines and Pyrimidines Substituted with Chiral Acyclic Chains by Sugar-Ring Opening of [alpha]-L-Arabinopyranosyl Nucleosides," J. Chem. Soc., Perkin Transactions 1, 1992(15), 1943-1952 (Aug. 7, 1992); supplied by applicant.*

(Continued)

*Primary Examiner*—L. E. Crane (74) *Attorney, Agent, or Firm*—King & Spalding (57) ABSTRACT

Method for the sterospecific preparation of 2' or 3' deoxy and 2',3'-dideoxy-β-L-pentafuranonucleoside compounds. 2' or 3' deoxy and 2',3'-dideoxy-β-L-pentofuranonucleoside compounds are also described. Finally, the invention concerns the use of these compounds, and particularly 2',3'dideoxy-β-L-fluorocytidine, as drugs, and especially as anti-viral agents.

10 Claims, 2 Drawing Sheets

U.S. PATENT DOCUMENTS

| | | | |
|---|---|---|---|
| 5,543,390 A | | 8/1996 | Yatvin et al. |
| 5,543,391 A | | 8/1996 | Yatvin et al. |
| 5,554,728 A | | 9/1996 | Basava et al. |
| 5,559,101 A | * | 9/1996 | Weis et al. ............... 514/45 |
| 5,561,120 A | * | 10/1996 | Lin et al. ................ 514/49 |
| 5,587,362 A | | 12/1996 | Chu et al. |
| 5,587,480 A | | 12/1996 | Belleau et al. |
| 5,627,160 A | * | 5/1997 | Lin et al. ................ 514/49 |
| 5,631,239 A | * | 5/1997 | Lin et al. ................ 514/49 |
| 5,770,713 A | | 6/1998 | Imbach |
| 5,770,725 A | | 6/1998 | Gosselin et al. |
| 5,830,881 A | * | 11/1998 | Lin et al. ................ 514/45 |
| 5,849,905 A | | 12/1998 | Gosselin et al. |
| 6,025,335 A | * | 2/2000 | Weis et al. ............... 514/44 |

FOREIGN PATENT DOCUMENTS

| | | |
|---|---|---|
| EP | 0 285 884 A2 | 10/1988 |
| EP | 0285884 * | 10/1988 |
| EP | 0352248 * | 7/1989 |
| EP | 0 337 713 B1 | 10/1989 |
| EP | 0 350 287 A2 | 1/1990 |
| EP | 0 352 248 A1 | 1/1990 |
| EP | 0 375 329 A2 | 6/1990 |
| EP | 0 382 526 A2 | 8/1990 |
| EP | 0 433 898 A2 | 6/1991 |
| EP | 0 494 119 A1 | 7/1992 |
| EP | 0 515 144 A1 | 11/1992 |
| EP | 0 515 156 A1 | 11/1992 |
| EP | 0 515 157 A1 | 11/1992 |
| EP | 0 526 253 A1 | 2/1993 |
| WO | WO 88/07532 A1 | 10/1988 |
| WO | WO 88/08001 A1 | 10/1988 |
| WO | WO 89/02733 A1 | 4/1989 |
| WO | WO 90/00555 A1 | 1/1990 |
| WO | WO 90/12023 A1 | 10/1990 |
| WO | WO 91/11186 A1 | 8/1991 |
| WO | WO 91/16920 A1 | 11/1991 |
| WO | WO 91/17159 A1 | 11/1991 |
| WO | WO 91/18914 A1 | 12/1991 |
| WO | WO 91/19721 A1 | 12/1991 |
| WO | WO 92/00315 A1 | 1/1992 |
| WO | WO 92/06102 A1 | 4/1992 |
| WO | WO 92/08717 A1 | 5/1992 |
| WO | WO 92/08727 A1 | 5/1992 |
| WO | WO 92/10496 A1 | 6/1992 |
| WO | WO 92/10497 A1 | 6/1992 |
| WO | WO 92/14729 A1 | 9/1992 |
| WO | WO 92/14743 A2 | 9/1992 |
| WO | WO 92/15308 A1 | 9/1992 |
| WO | WO 92/18517 A1 | 10/1992 |
| WO | WO 92/21676 A1 | 12/1992 |
| WO | WO 93/00910 A1 | 1/1993 |
| WO | WO 93/12128 A1 | 6/1993 |
| WO | WO 93/12131 A1 | 6/1993 |
| WO | WO 93/12132 A1 | 6/1993 |
| WO | WO 93/24510 A1 | 12/1993 |
| WO | WO 94/04154 A1 | 3/1994 |
| WO | WO 94/05300 A1 | 3/1994 |
| WO | WO 94/09793 A1 | 5/1994 |
| WO | WO 94/14456 A1 | 7/1994 |
| WO | WO 94/14802 A1 | 7/1994 |
| WO | WO 94/26273 A1 | 11/1994 |
| WO | WO 94/26764 A1 | 11/1994 |
| WO | WO 94/27616 A1 | 12/1994 |
| WO | WO 95/07086 A1 | 3/1995 |
| WO | WO 95/07287 A1 | 3/1995 |
| WO | WO 95/11252 A1 | 4/1995 |
| WO | WO 95/20595 A1 | 8/1995 |
| WO | WO 96/15132 A1 | 5/1996 |
| WO | WO 96/40164 A1 | 12/1996 |

OTHER PUBLICATIONS

Asseline, et al., "Synthesis and Physicochemical Properties of Oligonucleotides built with either alpha-L or beta-L Nucleotides Units and Covalently Linked to an Acridine Derivative," *Nucleic Acids Res.*, 19 (15):4067-4074 (1991).

Ayoola, et al., "Progress in the Control of Viral Hepatitis: Memorandum from a WHO Meeting," *Bulletin of the World Health Organization*, 66(4):443-455 (1988).

Balzarini, J., "Potent and selective anti-HTLV-III/LAV activity of 2', 3'-dideoxycytidinene, the 2',3'-unsaturated derivative of 2',3'-dideoxycytidine," et al., *Biochem. Biophys. Res. Comm.*, 140(2): 735-742 (Oct. 30, 1986).

Beach, J. W., et al., "Synthesis of EnantiomericallyPure (2'R,5'S)-(−)-I-[2 (hydroxymethyl)-oathiolan-5-yl]Cytosine . . . ," *J. Org. Chem.*, 57:2217-2219 (1992).

Beasley, et al., "Hepatocellular Carcinoma and Hepatitis B Virus," *The Lancet*, 1129-1133 (1981).

Belleau, B., et al., "Design and Activity of a Novel Class of Nucleoside Analogs . . . ," *Intl. Conf. on AIDS*, Montreal, Quebec, Canada, Jun. 4-9, 1989.

Boutelje, et al., *Chemical Abstracts*, 108:128048 (1987).

Carter et al., "Activities of (−)-carbovir and 3'-azido-3'-deoxythymidine against human immunodeficiency virus in vitro," *Antimicrob. Agents Chemother,*, 34(6):1297-1300 (Jun. 1990).

Chang, C., et al., "Production of Hepatitis B Virus in vitro by Transient Expression . . . ," *EMBO J.*, 6(3):675-680 (1987).

Chang, C.-N., et al., "Deoxycytidine Deaminase-resistant Steroisomer is the Active Form of (+)-2'-3'-Thiacytidine in the Inhibition of Hepatitis B Virus Replication," *J. Biol. Chem.*, 267(20):13938-13942 (1992).

Chang, C-N., et al., "Biochemical Pharmacology of (+) and (−)-2',3'-Dideoxy-3'Thioacytidine as Anti-Hepatitis B Virus Agents," *J. Biol. Chem.*, 267(31):22414-22420 (1992).

Chu, C.K., et al., "An Efficient Total Synthesis of 3'-Azido-3'-Deoxythiymidine (AZT) and 3'-Azido-2',3'-Dideoxyuridine (AZDDU, CS-87) from D-Mannitol," *Tetrahedron Lett.*, 29(42):5349-5352 (1988).

Chu, et al., "Structure Activity Relationships of Pyrimide Nucleosides as Antiviral Agents for Human Immunodeficienty Virus Type 1 in Peripheral Blood Mononuclear Cells." *J, Med. Chem.*, 32:612 (1989).

Chu, et al., "Asymmetric Synthesis of Enantiomerically Pure (−)-(1'R,4'R)-Dioxolane-thymine and Its Anti-HIV Activity," *Tetrahedron Letters*, 32(31):3791-3794 (1991).

Chu, et al., "Comparative Activity of 2',3'-Saturated and Unsaturated Pyrimidine and Purine Nucleosides . . . ," *Biochem. Pharm.* 37(19):3543-3548 (1988).

Chu, et al., "Enantiomeric Synthesis of (+)-BCH-189[(+)-(2S,5R)-1-(Hydroxymethyl) 1,3-oxathiolane-5-yl]cytosine]from D-Mannose and Its Anti-HIV Activity," *J. Org. Chem.*, 56:6503-6505 (1991).

Chu, et al., "Synthesis and Anti-HIV and Anti-HBV Activity of Enantiomerically Pure Oxathiolane Nucleosides," *Antiviral Research*, 17(S1):2 (Mar. 1992).

Chu, et al., "Synthesis and Biological Evaluation of D-(2S) and L-(2R)-I,3 Oxathiolanyl-and D-(2R)- and L-(2S)-1,3-Dioxolanyl-Nucleosides as Anti-HIV and Anti-HBV Agents," *Antiviral Research*, 30(S1):192 (Apr. 1993).

Coates, J., et al., "The Separated Enantiomers of 2'-deoxy-3'-thiacytidine (BCH-189) Both Inhibit Human Immunodeficiency Virus Replication In Vitro," *Antimicrob. Agents Chemother.* 36(1):202-205 (1992).

Cretton, E., et al., "Catabolism of 3'-Azido-3'-Deoxythymidine in Heptaocytes and Liver Microsomes, with Evidence of Formation of 3'-Amino-3'-Deoxythymidine a Highly Toxic Catabolite for Human Bone Marrow Cells," *Molecular Pharmacology*, 39:258-266 (1991).

Cretton, E., et al., "Pharmokinetics of 3'-Azido-3'-Deoxythymidine and its Catabolites and interactions with Probenecid in Rhesus Monkeys," *Antimicrobial Agents and Chemotherapy*, 35(5):801-807 (1991).

Di Bisceglie, A.M., et al., "Hepatocellular Carcinoma," NIH Conference, *Annals of Internal Medicine*, 108:390-401 (1988).

Doong, S.-L., et al., "Inhibition of the Replication of Hepatitis B virus in vitro by 2',3'-Dideoxy-3'-Thiacytidine and Related Analogues," *Natl. Acad. Sci. USA*, 88:8495-8499 (1991).

Furman, et al., "The Anti-Hepatitis B Virus Activities, Cytotoxicities, and Anabolic Profiles of the (−) and (+) Enantiomers of *cis*-5-Fluoro-1-[2-(Hydromethyl)-1,3-Oxathiolane-5-yl) Cytosine," *Antimicrob. Agents and Chemo.*, 36(12):2686-2692 (1992).

Ganem, "Animal Models of Hepatitis B Virus," *Experimental Models in Antimicrobial Chemotherapy*, 2:259-272 (1986).

Ganem, D., et al., "The Molecular Biology of the Hepatitis B Viruses," *Ann. Rev. Biochem.*, 56:651-693 (1987).

Gosselin, et al, "Improved and New Synthetic Procedures, Methods, and Techniques," *Nucleic Acid Chemistry*, PJ4, L. B. Townsend and R. S. Tipan, eds, John Wiley & Sons, Inc. (1991), p. 41.

Gosselin, G., "Enantiomeric 2',3'-Deoxycytidine Derivatives are Potent Human Immunodeficiency Virus Inhibitors in Cell Cultures," *Compt.Rend.. Acad. Sci. Paris Sci. Vie.* 317:85-89 (1994).

Hamamoto, Y., et al., "Inhibitory effect of 2',3'-didehydro-2',3'-dideoxynucleosides on infectivity, cytopathic effects, and replication of human immunodeficiency virus," *Antimicrob. Agents. Chemother.*, 31(6):907 (Jun. 1987).

Hoong, et al., "Enzyme-Mediated Enantioselective Preparation of Pure Enantiomers of the Antiviral Agent 2'3'-Dideoxy-5-Fluoro-3'-Thiacytidine (FTC) and Related Compounds," *J. Org. Chem.*, 57:5563-5565 (1992).

Jeong, et al., "An Efficient Synthesis of Enantiomerically Pure (+)-(2S,5R)-1-[2-(Hydroxymethyl)-1,3-oxathiolan-5-y;]cytosine[(+)-BCH-189] from D-Galactose," *Tetrahedron Letters*, 33(5):595-598 (1992).

Jeong, L., et al., "Asymmetric Synthesis and Biological Evaluation of β-L-(2R,5S)-and a-L-(2R-5R)-1,3-Oxathiolane-0Pyrimidine and -Purine Nucleosides ad Potential Anti-HIV Agents," *J. Med. Chem.*, 36(2):181-195 (1993).

Jones & Bischofberger, "Minireview: nucleotide prodrugs," *Antiviral Research*, 27:1-17 (1995).

Jurovcik & Holy, "Metabolism of pyrimidine L-nucleosides," *Nucleic Acid Research*, 3(8):2143-2154 (1976).

Kassianides, C., et al., "Inhibition of Duck Hepatitis B Virus Replication by 2',3'-Dideoxycytidine," *Gastroenterology*, 97(5):1275-1280 (1989).

Kim, et al., "L-β-(2S,4S)-and L-α-(2S,4R)-Dioxolanyl Nucleosides as Potential Anti-HIV Agents: Asymmetric Synthesis and Structure-Activity Relationships," *J. Med. Chem.*, 36(5):519-528 (1993).

Kim, H.O., et al., "1,3-Dioxolanylpurine Nucleosides (2R,4R) and (2R,4S) with Selective Anti-HIV-1 Activity in Human Lymphocytes," *J. Med. Chem.*, 36(1):30-37 (1993).

Kim, H.O., et al., "Potent Anti-HIV and Anti-HBV Activities of (−)-L-β-Dioxolane-C and (+)-L-β-Dioxolane-T and Their Asymmetric Syntheses," *Tetrahedron Lett.*, 33(46):6899-6902 (1992).

Krenitsky, T.A., et al., "3'-Amino-2'3'-Dideoxyribonucleosides of Some Pyrimidines: Synthesis and Biological Activities," *J. Med. Chem.*, 26(6) 891-895 (1983).

Kukhanova, M., et al., "L-and D-Enantiomers of 2',3'-Dideoxycytidine 5'-Triphosphate Analogs as Substrates for Human DNA Polymerases," *J. Biol. Chem.*, 270(39):23056-23059 (1995).

Lee, B., et al., "In Vitro and In Vivo Comparison of the Abilities of Purine and Pyrimidine 2',3'-Dideoxynucleosides To Inhibit Duck Hepadnavirus," *Antimicrob. Agents and Chemother.*, 33(3):336-339 (1989).

Lin, et al., "Potent and Selective In Vitro Activity of 3'-Deoxythmindine-2-Ene-(3'-Deoxy-2',3'-Didehydrothymidine) Against Human Immunodeficiency Virus," *Biochem. Pharm.* 36(17):2716 (1987).

Mahmoudian, M., et al., "Enzymatic Production of Optically Pure (2'R-cis)-2;-deoxy-3'tiacytidine (3TC,Lamivudine): A Potent Anti-HIV Agent," published by the Glaxo Group Research ltd., *Enzyme Microb. Technol.*, 15:749-755 (1993).

Mansuri, M.M., et al., "Preparation of the Geometric Isomers of DDC, DDA, D4C, and D4T . . . ", *Bioorg. Med. Chem. Lett.*, 1:65-68 (1991).

Matthes, E., et al., "Potent Inhibition of Hepatitis B Virus Production in Vitro by Modified . . . ," *Antimicrob. Agents and Chemo.*, 34(10):1986-1990 (1990).

Miller, R.H., et al., "Common Evolutionary Origin of Hepatitis B Virus and Retroviruses," *Proc. Natl. Acad. Sci. USA*, 83:2531-2535 (1986).

Mitsuya, H., et al., "3'-Azido-3'-Deoxythymidine (BW A 509U): An antiviral Agent that Inhibits and Infectivity and Cytopathic Effect of Human T-Lymphotropic Virus type III/Lymphadenopathy-Associated Virus in Vitro," *Proc. Natl. Acad. Sci. USA*, 82:7097-7100 (1985).

Mitsuya, H., et al., "Molecular Targets for AIDS Therapy," *Science*, 249:1533-1544 (1990).

Mitsuya, H., et al., "Rapid in Vitro Systems for Assessing . . . ," *AIDS: Modern Concepts and Therapeutic Challenges*, S. Broder, Ed. pp. 303, Marcel-Dekker, New York (1987).

Norbeck, D., et al., "A New 2'3'-Dideoxynucleoside Prototype with In Vitro Activity Against HIV," *Tetrahedron Lett*, pp. 6263-6266 (1989).

Norin, *Chemical Abstracts*, 108:146380 (1987).

Ohno, et al., *Chemical Abstracts*, 112:194612 (1989).

Okabe, M., et al., "Synthesis of the Dideoxynucleosides ddC and CNT from Glutamic Acid, Ribonolactone, and Pyrimidine Bases," *J. Org. Chem.* 53(20): 4780-4786, (1988).

Pai, S.B., et al., "Inhibition of Hepatitis B Virus by a Novel L-Nucleoside, 2'-Fluoro-5-Methyl-β-L-Arabinofuranosyl Uracil," *Antimicrobial Agents and Chemotherapy*, 40(2):380-386 (1996).

Perigaud, C., et al., "Equal Inhibition of the Replication of Human Immunodeficiency Virus in Human T-cell Culture by ddA Bis( SATE )phosphotriester and 3'-Azido-2',3'-dideoxythymidine," *Biochem. Pharmacol.* 48(1):11-14 (Jul. 5, 1994).

Piantadosi, C., et al., "Synthesis and evaluation of novel ether lipid nucleoside conjugates for anti-HIV-1 activity," *J. Med. Chem.*, 34(4):1408-1414 (Apr. 1991).

Richman, D.D., et al., "The Toxicity of Azidothymidine (AZT) in the Treatment of patients with AIDS and AIDS-related complex. A Double-blind, Placebo-controlled Trial," *N. Eng. J. Med.*, 317(4):192-197 (Jul. 23, 1987).

Ryan, K.J. et al., 9-β-L-Riboufuranosyladenine ("L-Adenosine"), *Synthetic Procedures in Nucleic Acid Chemistry*, vol. 1, pp. 163-167, Interscience Publishers, New York, NY (1968).

Satsumabayashi, S. et al., "The Synthesis of 1,3-Oxathiolane-5-one Derivatives," *Bull, Chem. Soc.* Japan, 45:913-915 (1972).

Schinazi, et al., "Pure Nucleoside Enantiomers of β-2',3'-Dideoxycytidine Analogs are Selective Inhibitors of Hepatitis B Virus in Vitro," *Antimicrob. Agents and Chemother.*, 38(9):2172-2174 (1994).

Schinazi, R.F., et al., "Comparison of inhibitory activities of various antiretroviral agents against particle-derived and recombinant human immunodeficiency virus type 1 reverse transcriptases," *Antimicrob. Agents Chemother*, 33(1):115-117 (Jan. 1989).

Schinazi, R.F. et al., "Activities of the Four Optical Isomers of 2',3"-Dideoxy-3'-Thiacytidine . . . ," *Antimicrob. Agents & Chemo.*, 36(3):672-676 (1992).

Schinazi, R.F., et al., "Insights into HIV Chemotherapy," *AIDS Research and Human Retroviruses* 8(6):963-989 (1992).

Schinazi, R.F., et al., "Pharmacokinetics and Metabolism of Racemic 2',2'-Dideoxy-5 . . . ," *Antimicrob. Agents and Chemother.*, 36(11)2432-2438 (1992).

Schinazi, R.F., et al., "Rapid Communications: Substrate Specificity of *Escherichia coli*, Thymidine Phosphorylase for Pyrimidine Nucleoside with an Anti-Human Immunodeficiency Virus Activity," *Bioch. Pharm.*, 44(2):199-204 (1992).

Schinazi, R.F., et al., "Selective Inhibition of Human Immunodeficiency Viruses by Racemates and Enantiomers of cis-5-Fluoro-1-[2-(Hydroxymethyl)-1,3-Oxathiolan-5-yl) Cytosine," *Antim. Agents and Chemo.*, 36(11):2423-2431 (1992).

Sells, M.A., et al., Production of Hepatitis B Virus Particles in Hep G2 Cells, *Proc. Natl, Acad. Sci. USA*, 84:1005-1009 (1997).

Soudeyns, H., et al., "Anti-Human Immunoodeficiency Virus Type 1 Activity and Vitro Toxicity of 2'-Deoxy-3'-Thiacytidine . . . ," *Antimicrob. Agents and Chemother.*, 35(7):1386-1390 (1991).

Spadari, et al., "L-Thymidine Is Phosphorylated by Herpes Simplex Virus Type 1 Thymidine Kinase and Inhibits Viral Growth" *J. Med. Chem.*, 35: No. 22, 4214-4220, (1992).

St. Clair, M.H., et al., "3'-Azido-3'-deoxythymidine triphosphate as an inhibitor and substrate of purified human immunodeficiency virus reverse transcriptase," *Antimicrob. Agents Chemother.*, 31(12):1972-1977 (Dec. 1987).

Sterzycki, R.Z. et al., "Synthesis and Anti-HIV Activity of Several 2'-Fluoro-Containing Pyrimidine Nucleosides," *J. Med. Chem.*, 33(8):2150-2157 (1990).

Storer, R., et al., "The Resolution and Absolute Stereochemistry of the Enantiomers of cis-1-[2-(Hydromethyl)-1,3-Oxathiolan-5-yl)cytosine (BCH-189): Equipotent Anti-HIV Agents," *Nucleosides & Nucleotides*, 12(2):225-236 (1993).

Su, T.-A., et al., Nucleosides. 136. Synthesis and Antiviral Effects and Several 1-(2-Deoxy-2-Fluoro-β-D-Arabinofuranousyl)-5Alkyluracils. Some Structure- Activity Relationships, *J. Med. Chem.*, 29(1):151-154 (1986).

Sureau, C., et al., "Production of Hepatitis B Virus by a Differentiated Human Hepatoma Cell Line after Transfection with Cloned Circular HBV DNA," *Cell*, 47:37-47 (1986).

Tsurimoto, T., et al., "Stable Expression and Replication of Hepatitis B Virus Genome . . . ," *Proc. Natl, Acad. Sci. USA*, 84:444-4448 (1987).

Volk, W.A., editor, "Hepatitis," *Essentials of Medical Microbiology*, J.B. Lippincott Company, (Philadelphia/Toronto) 2nd Ed., pp. 609-618 (1982).

Vorbrüggen, et al., "Nucleoside Synthesis with Trimethylsily Triflate and Perchlorate as Catalyst," *Chem. Ber.*, 114:1234-1255 (1981).

Watanabe, K.A., et al., "Synthesis and anti-HIV-1 activity of 2'-"up"-fluoro analogues of active anti-AIDS nucleosides 3'-azido-3'-deoxythymidine (AZT) and 2',3'-dideoxycytidine (DDC)," *J. Med. Chem.*, 33(8):2145-2150 (Aug. 1990).

Wilson, L.J., et al., "A General Method for Controlling Glycosylation Sterochemistry in the Synthesis . . . ," *Tetrahedron Lett.*, 31(13):1815-1818 (1990).

Wilson, L.J., et al., The Synthesis and Anti-HIV Activity of Pyrimidine Dioxolanyl Nucleosides, *Bioorganic & Medicinal Chemistry Letters*, 3(2):169-174 (1993).

Yokota et al., "Comparative Activities of Several Nucleoside Analogs Against Duck . . . ," *Antimicrob. Agents and Chemother.*, 34(7):1326-1330 (1990).

Zhu, Z., et al., "Cellular Metabolism of 3'-Azido-2',3'-Dideoxyuridine with Formation of 5'-O-Diphosphohexase . . . " *Molecular Pharmacology*, 38:929-938 (1990).

\* cited by examiner

FIG. 1

Legend to Figure 1
Scheme I: Bases = purines or pyrimidines, optionally appropriately protected; R = Benzoyl (Bz), acetyl (Ac), monomethoxytrityl (mMTr), or tert-butyldiphenylsilyl Scheme II

FIG. 2

2' OR 3'-DEOXY AND 2', 3'-DIDEOXY-β-L-PENTOFURANONUCLEO-SIDE COMPOUNDS, METHOD OF PREPARATION AND APPLICATION IN THERAPY, ESPECIALLY AS ANTI-VIRAL AGENTS

CROSS-REFERENCE TO RELATED APPLICATIONS

This application is a continuation of U.S. Ser. No. 09/953,187, filed Sep. 14, 2001, now abandoned, which is a continuation of, and claims priority to U.S. Ser. No. 08/612,965, filed Jul. 29, 1997, now abandoned, the disclosures of which are incorporated by reference.

The subject of the present invention is a method for the stereospecific preparation of 2'- or 3'-deoxy- and 2',3'-dideoxy-β-L-pentofuranonucleoside compounds.

The present invention also relates to 2'- or 3'-deoxy- and 2',3'-dideoxy-β-L-pentofuranonucleoside compounds.

The present invention finally relates to the use of these compounds as drugs and especially as antiviral agents.

Up until now, the synthesis and the biological evaluation of nucleoside analogs of the L configuration have been the subject of some studies, but until recently, the activities of most of the nucleosides were only associated with those of their D isomers [A. Holy, in Synthesis, Structure and Chemistry of Transfer Ribonucleic Acids and their Components (Proceedings of the International Conference Held in Dymaczewo near Poznan, Poland on Sep. 13-17, 1976), Polish Academy of Sciences, Poznan, 1976, p. 134, and references cited]. However, recently, β-L-Thymidine [S. Spadari, G. Mage, F. Focher, G. Ciarrocchi, R. Manserwigi, F. Arcamone, M. Capobianco, A. Carcuro, F. Colonna, S. Iotti and A. Garbesi, J. Med. Chem. 35, 4214 (1992)] and 2',3'-dideoxy-β-L-cytidine (β-L-DDC) [M. M. Mansuri, V. Farina, J. E. Starret Jr., D. A. Benigni, V. Brankovan and J. C. Martin, Bioorg. Med. Chem. Letters, 1, 65 (1991)] have been shown to exert a relatively limited antiviral activity in cell cultures against herpes simplex viruses (HSV) and the human immunodeficiency virus (HIV), respectively, the latter being the causative agent of the acquired immunodeficiency syndrome (AIDS).

In reality, β-L-DDC has been previously reported in a contradictory manner, on the one hand, to have no activity against HIV [M. Okabe, R. C. Sun, S. Y.-K. Tam, L. J. Todaro and D. L. Coffen, J. Org. Chem. 53, 4780 (1988)] and, on the other hand, to still exhibit a moderate activity against HIV [$IC_{50}$=0.66 $10^{-6}$M in a CEM cell culture: M. M. Mansuri, Y. Farina, J. E. Starret Jr., D. A. Benigni, V. Brankovan and J. C. Martin, Bioorg. Med. Chem. Letters, 1, 65 (1991)].

On the other hand, analogs of L isomers of AZT have been tested and have appeared to be inactive as anti-HIV agent [J. Org. Chem. 56, 3591 (1991)].

Accordingly, in a β-L isomeric series, nucleotide analogs of the dioxolanyl type [H. O. Kim, R. F. Schinazi, K. Shanmuganathan, L. S. Jeong, J. W. Beach, S. Nampalli, D. L. Cannon and C. K. Chu, J. Med. Chem. 36, 519 (1993) and references cited] and of the oxathiolanyl type [L. S. Jeong, R. F. Schinazi, J. W. Beach, H. O. KIM, S. Mampalli, K. Shanmuganathan, A. J. Alues, A. McMillan, C. K. Chu and R. Mathis, J. Med. Chem. 36, 181 (1993), and references cited] have been proposed and have been found to exhibit an anti-HIV activity.

The present invention provides new compounds which are nucleoside analogs with β anomers and which are of L configuration. Among these L enantiomers, a small number of examples of β-L-2',3'-dideoxynucleosides have been reported in the literature, but are based on methods of synthesis always involving a separation of the α anomers. [Patent EP 352 248 A1 24 Jan. 1990 (CA: 113(5), 41231 w (1990)]; Patent EP 285 884 A2 12 Oct. 1988 (CA: 111 (3), 23911x (1989)] and/or of their D enantiomers. [Patent JP 02 069 469 A2, 8 Mar. 1990 (CA: 115(1), 8560w (1991)]; Patent JP 0 222 9192 A2, 11 Sep. 1990 [CA: 114(11), 102709c (1991)]; Patent JP 0206 9476 A2 8 Mar. 1990 [CA: 113(11), 97977m (1990)]; L. Kaulina, E. Liepins, M. Lidaks and R. A. Zhuk, Khim. Geterstsikl-Soedin. (1), 101 (1982) [CA: 96(17), 143 248e (1982)], which are obtained concomitantly, such that their stereo-specificity or their isomeric purity can be questioned.

In particular, Patent EP 352 248 describes a method of synthesis by condensation of a sugar and a purine or pyrimidine base.

However, in Patent EP 352 248, the initial sugar compound has a hydrogen and a halogen at the 2' position, such that the condensation with the base B leads to a mixture of α and β anomers.

The present invention provides a method which makes it possible to prepare stereospecifically the β-L-2',3'-dideoxynucleoside compounds. It appeared, after evaluation of their potential as antiviral agent, more particularly against HIV, that some of these stereoisomeric compounds were particularly active.

The subject of the present invention is therefore firstly a method for the preparation of 2'- or 3'-deoxy- and 2',3'-dideoxy-β-L-pentofuranonucleoside compounds of formula I:

in which
B represents a purine or pyrimidine base;
$R_1$ represents OH;
$R_2$ and $R_3$ represent, independently of each other, H or OH;
at least one of $R_2$ and $R_3$ represents H;
characterized in that the following steps are carried out:
1) a compound of formula (II) is condensed with the base B in order to obtain the compound of formula (III)

in which in formulae (II) and (III)
$R'_1$ and $R'_2$ have the meanings given for $R_1$ and $R_2$ except that when $R_1$ and $R_2$ represent OH, the said OH group is protected by a protecting group such as an acyl, benzoyl, benzyl or silyl group, R'$_3$ represents a C$_1$ to C$_5$ alkyl group or a phenyl radical, which are optionally substituted, X is a leaving group such as Cl, Br, I or a C$_1$ to C$_5$ acyloxy or alkoxy group, B' is a purine or pyrimidine base B which is optionally appropriately protected, 2) the R'$_3$CO group at the 2' position is removed by deacetylation so as to obtain an OH group and a compound of formula (IV)

3) optionally, the OH group at the 2' position is removed;

4) where appropriate, the R'$_1$ and R'$_2$ groups and the B' base are deprotected so as to obtain the compounds of formula (I).

The presence of an acyl protection at the 2' position causes a stereospecific coupling with the heterocyclic base leading stereospecifically to the β anomer of the nucleoside during the glycosylation according to the Baker "trans" rule, because it induces the formation of an intermediate acyloxonium.

Any heterocyclic base can be condensed with the sugar (II). There may be mentioned in particular B represents one of the adenine, guanine, hypoxanthine, uracil, thymine or cytosine bases, it being possible for these bases to be substituted especially by halogen at the 5 position for uracil and cytosine.

For each type of base, the conditions for glycoside condensation in nucleoside synthesis are numerous and well known to persons skilled in the art.

Instead of the above step 3) for removal, a substitution of the OH group by an N$_3$, F or NH$_2$ group can be carried out with, in this case, an inversion of configuration on the carbon considered. Compounds of formula (I) are obtained in this case with R$_2$=N$_3$, F or NH$_2$ with the inverse configuration to that represented in formula (I).

Preferably, in the compounds (II) and (III), R'$_3$ represents a C$_1$ to C$_5$ alkyl group, preferably CH$_3$.

Thus, the compounds (II) can be prepared in which the compound (II), di-O-acetylated at the 1,2 position, in which X and R'$_3$COO represent an O-acetyl group, is prepared by acetolysis of the 1,2-isopropylidene-L-xylofuranose compound of formula (V)

(V)

This reaction occurs in two stages:
a) in an acidic medium CH$_3$COOH 85% and H$_2$SO$_4$, then
b) with (CH$_3$CO)$_2$O in pyridine.

Preferably, R'$_2$ and R'$_3$COO are different, in particular R'$_2$ is an O-benzoyl group and R'$_3$COO is an O-acyl group.

Thus, it is possible to selectively deprotect the alcohol at the 2' position by means of hydrazine hydrate at step 2) above.

Figure 1:
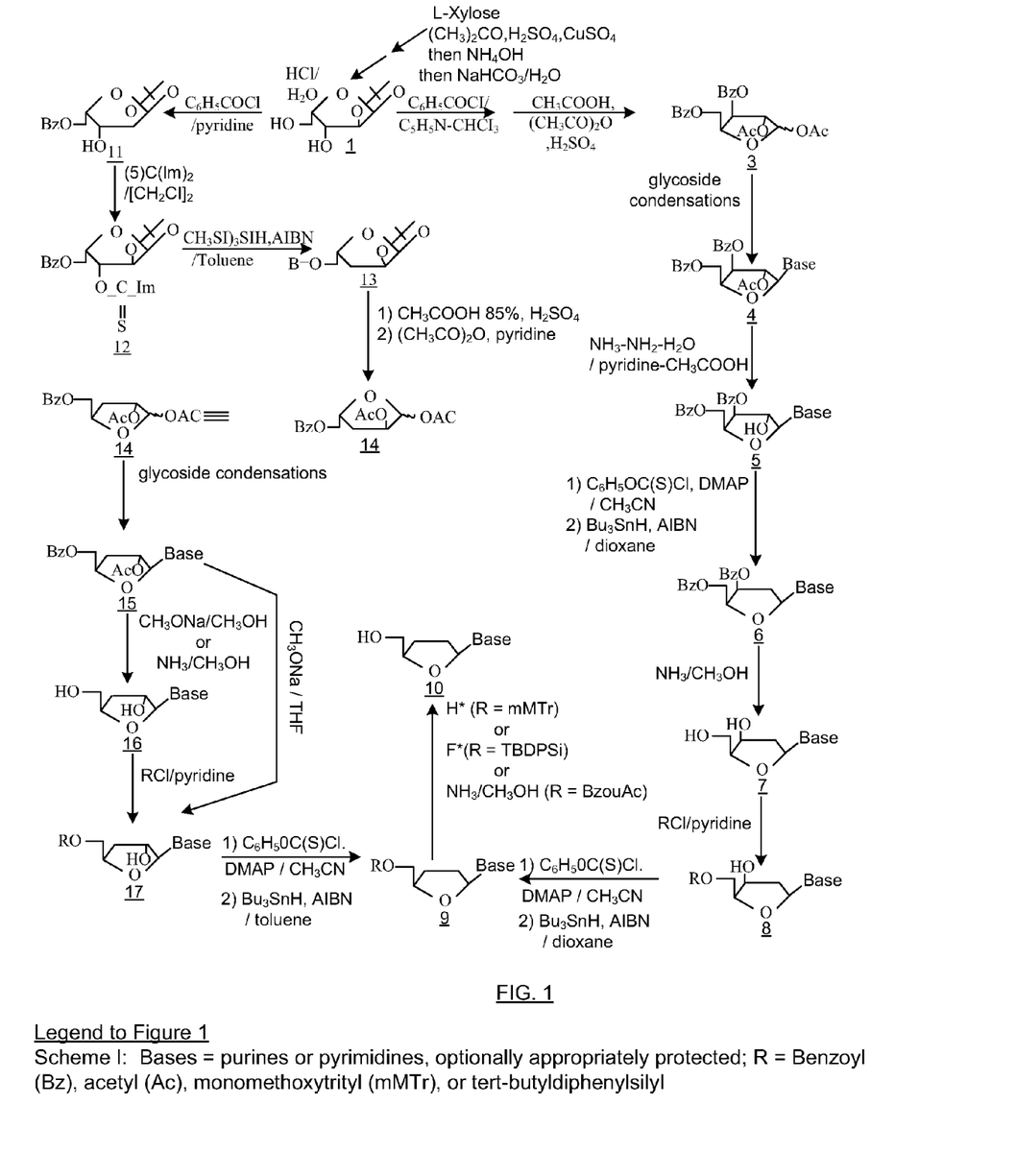
FIG. 1 shows a synthesis of compounds 1 and 3-17.

Scheme I outlines the various steps of the synthesis of compounds of formula (I) in which R$_2$ and R$_3$ represent H or OH by detailing the reaction conditions of persons skilled in the art. It is possible to introduce the compounds of formula (I) onto the N$_3$, F and NH$_2$ groups by substitution in place of the OH group with inversion of configuration.

In Scheme I, starting with commercial L-xylose, two synthesis routes are described, both involving the prior production of an L-pentofuranose (compounds 3 and 14) appropriately protected and possessing at the 2 position a participating O-acyl group inducing during glycosylation reactions the 1',2'-Trans geometry desired for the nucleoside obtained (B. R. Baker, in the Ciba Foundation Symposium on the Chemistry and Biology of the Purines, G. E. W. Wrolstentiolme and C. M. O'Connor Eds, Churchill London, p. 120 (1957)). The sugar 3 and 14 are obtained from L-xylose which is converted to 1,2-isopropylidene-L-xyloruranose, the acetolysis of which leads to the di-O-acetylated derivative at the 1,2 position.

Compound 1 is obtained in two stages from acetone in the presence of copper sulfate and then in acid medium.

Compound 1 is reacted with C$_6$H$_5$COCl in pyridine in order to obtain the one intermediate whose OH groups at the 5' and 3' positions are protected by a benzoyl. This protected intermediate is acetolyzed in acid medium (CH$_3$COOH 85%, H$_2$SO$_4$) and then in the presence of anhydride (CH$_3$CO)$_2$O in pyridine in order to give the compound 3.

The first synthesis route consists in condensing 1,2-di-O-acetyl-3,5-di-O-benzoyl-L-xylofuranose (3) with a heterocyclic base. The nature of the acetyl protecting group of the sugar 3 at the 2' position causes a stereospecific coupling leading to the β anomer. The protecting group at the 3' position being different, it is possible to then deacetylate selectively at the 2' position by means of hydrazine hydrate in pyridine in acid medium the completely protected β-L-xylofuranosyl-nucleoside 4 obtained, thus leading to the compound 5. The latter is then converted to its thiocarbonyl derivative which is subjected to a Barton-type deoxygenation reaction involving free radicals according to an experimental method which is already used in the D series (M. J. Robins, D. Nadej, F. Hansske, J. S. Wilson, G. Gosselin, M. C. Bergogne, J. L. Imbach, J. Balzarini and F. De Clercq, Can. J. Chem. 66, 1258 (1988)), in order to give the compound 6. The Barton reduction involving free radicals consists in substituting the hydrogen of the alcohol functional group by a C(S)X group (X=imidazole, phenoxy and the like) and then in reducing the ROC(S)X functional group by homolytic rupture by means of Bu$_3$SnH and AIBN. Compound 6 is debenzoylated in order to give the 2-deoxy-β-L-threopentofuranosylnucleoside 7. A selective protection of the 5' primary hydroxyl leads to the derivative 8 which is subjected to a deoxygenation at the 3' position according to the Barton-type method. Finally, the resulting compound 9 is deprotected at the 5' position in order to give the 2',3'-β-L-pentofuranosylnucleoside 10.

The second synthesis route involves the prior preparation of 1,2-di-O-acetyl-3-deoxy-5-O-benzoyl-L-erythropentofuranose (14), unpublished up until now. To do this, the 1,2-di-O-isopropylidene-α-L-xylofuranose (1), obtained in two stages from L-xylose and which is an intermediate in the synthesis of the sugar 3 used in the first route, is selectively benzoylated at the 5 position in order to give the compound 11. The latter is converted to its thiocarbonylated derivative 12 which is deoxygenated by means of trimethylsilylsilane (D. H. R. Barton, D. O. Jang and J. Cs. Jaszberenyi, Tetrahedron, 49, 2793 (1993)) in order to give the compound 13. This compound 13 is freed of acetone in aqueous acetic acid in the presence of sulfuric acid, and the resulting intermediate is not isolated, but directly acetylated using acetic anhydride in pyridine in order to give the desired sugar 14. The condensation of 14 with a purine or pyrimidine aglycone leads to the protected nucleoside 15 which can be either completely deacylated by means of sodium methoxide or ammonia in solution in methanol to give the 3-deoxy-β-L-erythropentofuanosylnucleoside 16, or be selectively deacetylated at the 2' position by means of sodium methoxide in THF in order to give the derivative 17. A deoxygenation reaction according to Barton on the 2'-thiocarbonylated derivative of 17 then leads to the derivative 9, which is identical to that obtained in the first synthesis route.

To illustrate the present invention, the preparation (according to the first synthesis route) and the characterization of 2'-3'-dideoxy-β-L-uridine (β-L-DDU), 10a) and that of 2',3'-dideoxy-5-fluoro-β-L-uridine (β-L-5-fluoro-DDU), 10b) are described in the examples which will be given below.

To prepare a compound of formula (I) in which B is cytosine, it is possible, according to the present invention, to prepare a compound of formula (I) where B is uracil, and then to convert the uridine derivative to a cytidine derivative by converting the uracil to cytosine.

Figure 2:
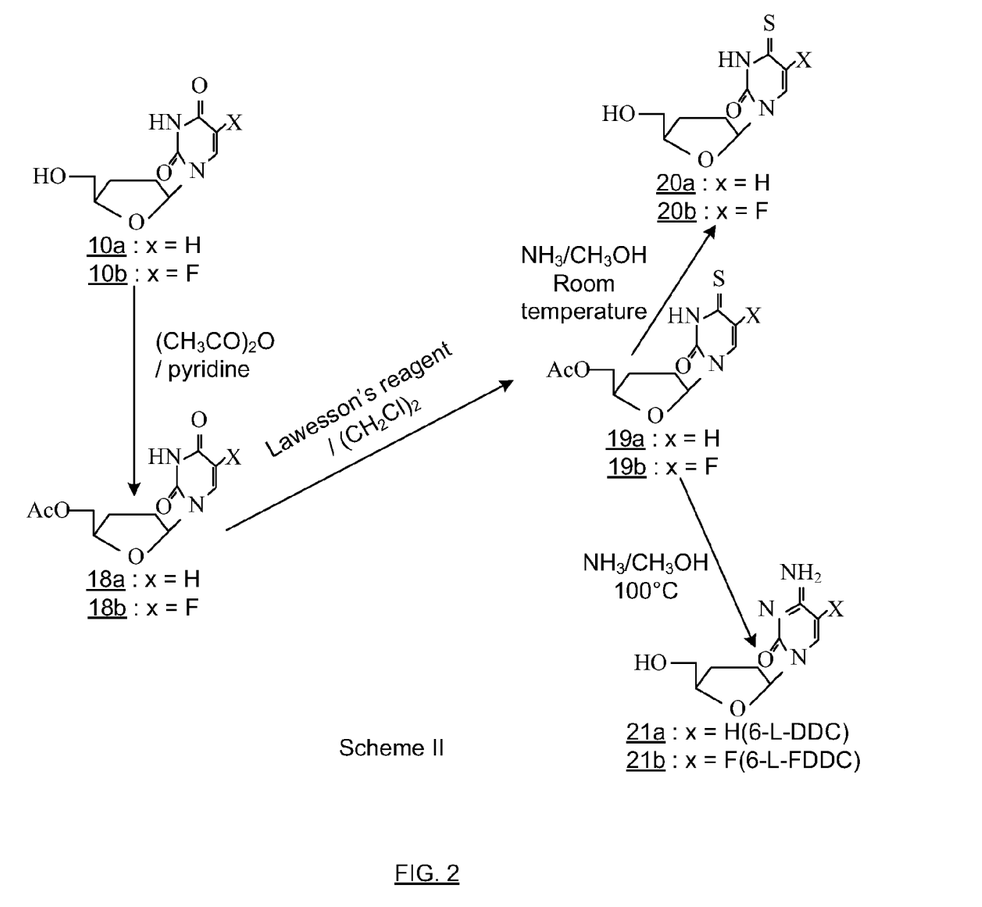
FIG. 2 shows a synthesis of compounds 18, 19, 20 and 21.

The experimental conditions are indicated in Scheme II which represents the conversion of β-L-DDU and β-L-5-fluoro-DDU. These two compounds are converted (Scheme II) to 2',3'-dideoxy-β-L-cytidine (β-L-DDC, 21a) and to 2',3'-dideoxy-β-L-5-fluorocytidine (β-L-5-fluoro-DDC, 21b), respectively.

The β-L-DDU (10a) and β-L-5-FDDU (10b) are selectively acetylated at the 5' position in order to give the compounds 18a, b. The latter are converted to their corresponding thioamide derivatives 19a, b by treatment with the Lawesson reagent at reflux in dichloroethane according to a method previously developed in the D series of uridine (J. E. Starrett, Jr., D. R. Tortolani, D. C. Baker, M. T. Omar, A. K. Hebbler, J. A. Wos, J. C. Martin and M. M. Mansuri, Nucleosides Nucleotides, 9, 885 (1990)). The compounds 19a, b are treated with ammonia in methanol either at room temperature, or at 100° C. in order to give, respectively, the desired 2',3'-dideoxy-β-L-4-thiouridine 20a and its 5-fluorinated derivative 20b, as well as β-L-DDC (21a) and β-L-5-FDDC (21b).

While the L isomers are considered to be less toxic than the D isomers, because apparently they do not cause the same mutations in reverse transcriptase, the negative results obtained in the prior art, as regards the antiviral activity of the compounds of the 2',3'-L-dideoxynucleoside type (absence of activity or low activity) could be linked to a defect in stereospecificity.

Indeed, the β-L-DCC (21a) and β-L-5-F-DDC (21b) which are obtained according to the present invention have been evaluated against HIV in cell cultures (see examples below) on which these two molecules proved active, with especially a very high antiviral activity for β-L-5-FDDC.

In addition, 2',3'-dideoxy-β-L-5-fluorocytidine appears to be active on strains which are resistant to AZT and to nevirapine, the latter being at present the subject of clinical trials.

The compounds, in which one of $R_2$ or $R_3$ is OH and the other is H, can constitute intermediate compounds which are useful in the synthesis of the 2',3'-dideoxy-β-L-nucleoside derivatives, variously substituted on the sugar, especially by $N_3$, F or $NH_2$ groups.

In particular, the 2'-deoxy compounds of "threo" configuration (see in particular Scheme I, the compounds 7) and the 3'-deoxy compounds of "erythro" configuration (see in particular Scheme I, the compounds 16 upon deoxygenation of their hydroxyl lead to the β-L-2',3'-dideoxynucleosides.

The subject of the present invention is also stereochemically pure steroisomeric β-L-pentofuranonucleoside compounds corresponding to the following formula in which
$R_1$ and B have the meanings given above, and either $R_2$ represents OH and $R_3$ represents H, or $R_2$ represents H and $R_3$ represents OH.

Indeed, the β-L-pentofuranonucleoside compounds described in the literature always comprise an inverse configuration 3' ribo instead of 3' xylo as in the present invention. There is no example which is described in the literature of compounds of formula (I) with $R_2$=H and $R_3$=OH.

There may be mentioned in particular the compounds for which B represents uracil, 5-fluorouracil, hypoxanthine, 5-fluorocytosine guanine or adenine.

The subject of the present invention is also 2',3'-dideoxy-β-L-pentofuranonucleoside compounds of formula (I) above, in which
$R_1$ represents OH
$R_2$ and $R_3$ represent H and
B represents uracil, guanine, hypoxanthine, 5-fluorouracil, 5-fluorocytosine.

The subject of the present invention is more particularly a compound chosen from β-L-ddU, β-L-5-fluoro-ddU, β-L-5-fluoro ddC.

Finally, the subject of the present invention is the use of the compounds according to the invention as drugs. These may be, depending on the cases, antibiotics, antitumor agents or antiviral, especially anti-HIV, agents. In particular, as regards the 2',3'-dideoxynucleoside compounds according to the invention, these are more particularly useful as antiviral agent.

The subject of the present invention is especially the therapeutic application in antiretroviral chemotherapy of β-L-5-F-DDC, more particularly as anti-HIV agent.

Further advantages and characteristics of the present invention will appear in the light of the examples which will be given below.

FIG. 1 represents Scheme I.
FIG. 2 represents Scheme II.

EXAMPLE 1

Preparation of 1,2-di-O-acetyl-3,5-di-O-benzoyl-L-xylofuranose (3)

The procedures and the materials used have been described in J. Chem. Soc., Perkin Trans. I 1943 (1992).

The L-xylose was bought from Interchim, France.

This compound 3 is prepared in four stages from L-xylose without purification of the intermediates.

According to the same experimental procedure as that described in Gosselin et al., Nucleic Acid Chemistry, Improved and New Synthetic Procedures, Methods and Techniques, PT4, L. B. Towsend and R. S. Tipan, eds. John Witey and Sons, Inc., 1991, p. 41.

The monomeric mixture of 3 was obtained in the form of a pale yellow syrup and a recrystallization from ethanol led to the pure α anomer (yield 26%) melting point 104-107° C.

NMR data (DMSO, d): δ 2.06 and 2.10 (2 s, H.3 each, 2 COCH$_3$), 4.50 (m, H2, H5, 5'), 4.85 (m, 1H, H.1), 5.54 (dd, 1H, H-2, J=4.6 and 5.79 Hz (t, 1H, H.3, J=6.3 Hz)), (6.43 d, 1H, H.1, J=4.6 Hz), 7.5-8.0 (m, 10H, 2 COC6H5); [α]$_D^{20}$ −125.2° (C) 1,3 CHCl$_3$]; mass spectrum: (FAB>0 3-nitrobenzyl alcohol matrix) m/z 443 [M+H]$^+$, 383 [383 [M−CH$_3$CO$_2$], 105 [C$_6$H$_5$C=0]

Calc. for C$_{22}$H$_{22}$O$_9$ (442.41): C, 62.44; H, 5.01. Found: C, 62.28; and H, 5.04.

EXAMPLE 2

Preparation of 1-(2-O-acetyl-3,5-di-O-benzoyl-β-L-xylofuranosyl)uracil (4)

Hexamethyldisilazane (1.9 ml; 9.01 mmol), tri-methylchlorosilane (1.15 ml; 9.06 mmol) and tin (IV) chloride (1.59 ml; 13.5 g mmol) were added successively to a mixture of uracil (1.27 g; 11.33 mmol) and protected sugar (3) (5.0 g; 11.30 mmol), in anhydrous acetonitrile (170 ml). The clear solution obtained was stirred at room temperature for 24 hours. The reaction mixture was concentrated to a reduced volume, then diluted with chloroform (150 ml) then washed twice with the same volume of a solution of aqueous sodium hydrogenate carbonate and finally with water. The organic layers were dried over sodium sulfate, filtered on celite and then evaporated. The product obtained was purified on a silica gel chromatography column [eluent: gradient of methanol (0.4%) in methylene chloride] to give the pure compound 4 (3.709, 66%).

GENERAL CONDITIONS AND INSTRUMENTATION USED: They are identical to those reported by C. Périgaud, G. Gosselin and J.-L. Imbach, *J. Chem. Soc., Perkin Trans.* 1, 1943 (1992).

EXAMPLE 3

2',3'-Dideoxy-β-L-uridine (β-L-DDU, 10a)

1-(2-Deoxy-β-L-threo-pentofuranosyl)uracil (7a). A solution of 1-(3,5-di-O-benzoyl-β-L-xylofuranosyl)-uracil (6a) (1.4 g; 3.21 mmol) in ammoniacal methanol (previously saturated at 10° C. and hermetically closed) (90 ml) is stirred for two days at room temperature. The solution is evaporated several times with methanol under reduced pressure. The crude material obtained is dissolved in water and the resulting solution is washed several times with chloroform. The aqueous phase is evaporated and the residue is directly crystallized from methanol to give 0.6 g (yield 82%) of pure 7a: m.p.: 165-167° C.; $^1$H NMR (DMSO-d$_6$), δ ppm=11.23 (s, 1H, 3-NH), 7.92 (d, 1H H-6; J=8.1 Hz), 6.04 (dd, 1H, H-1'; J=2.0 and 8.3 Hz), 5.26 (d, H, H-5; J=8.1 Hz), 5.26 (d, 1H, OH-3'; J=3.2 Hz), 4.69 (t, 1H, OH-5'; J=5.3 Hz), 4.20 (m, 1H, H-3'), 3.81 (m, 1H, H-4'), 3.80-3.60 (m, 2H, H-5' and 5"), 2.6-2.5 (m, 1H, H-2', partially obscured by DMSO-d$_5$), 1.85 (dd, 1H, H-2"; J=2.0 and 14.7 Hz); mass spectra (matrix: glycerol-thioglycerol: 50:50, v/v): FAB>0 321 [M+glycerol+H]$^+$, 229 [M+H]$^+$, 117 [s]$^+$ and 113 [BH$_2$]$^+$; FAB<0 227 [M−H]$^-$.

Anal. Calculated for C$_9$H$_{12}$N$_2$O$_5$ (M=228.21): C, 47.36; H, 5.30; N, 12.28. Found: C, 47.45; H, 5.46; N, 12.12.

1-(5-O-Tert-butyldiphenylsilyl-2-deoxy-β-L-threo-pentofuranosyl)uracil (8a)

Tert-butyldiphenylsilane chloride (0.9 ml; 3.50 mmol) is added to a solution of 7a (0.6 g; 2.63 mmol) in anhydrous pyridine (8 ml). The solution is stirred for 4 h at room temperature and then the solvent is evaporated under reduced pressure. Water and dichloromethane are added. The organic phase is separated, washed successively with a saturated aqueous sodium hydrogen carbonate solution and water, dried over sodium sulfate and filtered. After evaporation to dryness, the residue is chromatographed on a silica gel column [eluent: step gradient of methanol (0-2%) in dichloromethane] to give 1.2 g (98%) of 8a in the form of a foam: $^1$H NMR (DMSO-d$_6$) δ ppm: 11.26 (s, 11H, 3-NH), 7.78 (d, 1H, H-6; J=8.2 Hz), 7.65-7.35 (m, 10 H, 2 C$_6$H$_5$), 6.09 (dd, 1H, H-1'; J=1.9 and 6.4 Hz), 5.55 (d, 1H, H-5; J=8.2 Hz), 5.30 (d, 1H, OH-3': J=3.1 Hz), 4.25 (m, H, H-3'), 4.05-3.95 (m, 2H, H-4' and 5'), 3.85-3.80 (m, 1H, H-5"), 2.6-2.5 (m, 1H, H-2' partially obscured by DMSO-d$_5$), 1.85 (dd, 1H, H-2"; J=1.9 and 16.5 Hz), 0.93 [s, 9H, (CH$_3$)$_3$C]; mass spectrum (matrix: glycerol-thioglycerol: 50:50, v/v): FAB<0 465 [M−H]$^-$ and 111 [B]$^-$.

5'O-Tert-butyldiphenylsilyl-2',3'-dideoxy-β-L-uridine (9a)

O-Phenylchlorothionoformate (0.68 ml; 5.02 mmol) and 4-dimethylaminopyridine (DMAP) (2.64 g; 21.6 mmol) are added to a solution of 8a (1.1 g; 2.36 mmol) in anhydrous acetonitrile (66 ml). The solution is stirred overnight at room temperature and then the solvent is evaporated under reduced pressure. Dichloromethane and water are added. The organic phase is separated and then washed successively with a 0.5M cooled aqueous solution of hydrochloric acid, water and a saturated aqueous solution of sodium hydrogen carbonate and again with water before being dried over sodium sulfate, filtered and evaporated to dryness. The residue (1.9 g) is dissolved in anhydrous dioxane, the resulting solution is evaporated under reduced pressure and this operation is repeated three times in order to give the crude thiocarbonate derivative. The latter is dissolved in dioxane (28 ml) and treated with tributyltin hydride (1.57 ml; 5.83 mmol) and α,α'-azobisisobutyronitrile (AIBN) (0.12 g; 0.73 mmol) at 90° C. for 2 h under argon. An additional quantity of Bu$_3$SnH (0.63 ml; 2.3 mmol) and of AIBN (50 mg; 0.30 mmol) is added and the heating is continued for 30 min. After evaporation of the solvent, dichloromethane and water are added. The organic phase is separated, dried over sodium sulfate and evaporated to dryness. The residue is chromatographed on a silica gel column [eluent: step gradient of methanol (0-5%) in dichloromethane] to give 0.54 g (yield 51%) of pure 9a which crystallizes from ethyl ether: m.p.=145-147° C.; UV [[EtOH 95] λmax 264 nm, λmin 235 nm; $^1$H NMR (DMSO-d$_6$) δ ppm: 11.29 (s, 1H, 3-NH), 7.74 (d, 1H, H-6), 7.65-7.40 (m, 10 H, 2 C$_6$H$_5$), 5.99 (dd, 1H, H-1'; J=3.1 and 7.4 Hz), 5.21 (d, 1H, H-5; J=8.1 Hz), 4.15-4.00 (m, 1H, H-4'), 3.94 (dd, 1H, H-5'; J=3.0 and 11.3 Hz), 3.75 (dd, 1H, H-5"; J=4.0 and 11.3 Hz), 2.45-2.20 (m, 1H, H-4'), 2.10-1.85 (m, 3H; H-2", 3' and 3"), 0.99 [s, 9H, (CH$_3$)$_3$C]; mass spectrum (matrix: glycerol-thioglycerol, 50:50, v/v) FAB>0 451 [M+H]$^+$, 339 [s]$^+$ and 113 [BH$_2$]$^+$.

2',3'-Dideoxy-β-L-uridin (β-L-ddU: 10a)

The compound 9a (0.25 g; 0.55 mmol) is dissolved in tetrahydrofuran (1.1 ml) and a 1.1M solution of tetra-n-butylammonium fluoride in THF (0.55 ml) is added. The solution is stirred for 2 h at room temperature and then evaporated under reduced pressure. Dichloromethane and water are added, and the aqeuous phase is evaporated to dryness. The residue is chromatographed on a silica gel column [eluent: step gradient of methanol (0-5%) in dichloromethane] to give 41 mg (yield 35%) of pure 10a which crystallizes from dichloromethane: m.p.=120-121° C.; UV [EtOH 95] max 262 nm, $\lambda$min 231 nm; $^1$H NMR (DMSO-$d_6$) $\delta$ ppm: 11.24 (s, 1H, 3-NH), 7.93 (d, 1H, H-6; J=8.1 Hz), 5.93 (dd, 1H, H-1'; J=3.4 and 6.7 Hz), 5.57 (d, 1H, H-5; J=8.1 Hz), 5.02 (poorly resolved triplet, 1H, OH-5'), 4.05-3.95 (m, 1H, H-4'), 3.70-3.40 [m, 2H, H-5' and 5"; after exchange $D_2O$: 3.63 ppm (dd, 1H, H-5'; J=3.4 and 12.1 Hz) and 3.49 (dd, 1H, H-5"; J=4.0 and 12.1 Hz), 2.35-2.20 (m, 1H, H-2'), 2.0-1.65 (m, 3H, H-2", 3' and 3"); mass spectra (matrix: glycerol-thioglycerol, 50:50, v/v); FAB>0 425 [2M+H]$^+$, 213 [M+H]$^+$, 113 [$BH_2$]$^{+\ and}$ 101 [s]$^+$; FAB<0 211 [M–H]$^-$ and 111 [B]$^-$.

EXAMPLE 4

2',3'-Dideoxy-$\beta$-L-5-fluorouridine ($\beta$-L-5-FDDU, 10b)

1-(2-Deoxy-$\beta$-L-threo-pentofuranosyl)-5-fluorouracil (7b)

A solution of 1-(3,5-di-O-benzoyl-2-deoxy-$\beta$-L-xylofuranosyl)-5-fluorouracil (6b) (0.25 g, 0.55 mmol) in ammoniacal methanol (25 ml) is stirred overnight at room temperature. The solution is evaporated under reduced pressure and the residue is evaporated several times with methanol. The crude material obtained is dissolved in water and the resulting solution is washed several times with chloroform. The aqueous phase is evaporated and the residue is directly crystallized from methanol to give 115 mg (yield 85%) of pure 7b: m.p.=198-200° C.; UV [EtOH 95] $\lambda$max 267 nm ($\epsilon$, 8500), $\lambda$min 233 nm ($\epsilon$, 2100); $^1$H NMR (DMSO-$d_6$) $\delta$ ppm=11.79 (s, 1H, 3-NH), 8.16 (d, 1H, H-6; J=7.4 Hz), 6.05 (dd, 1H, H-1'; J=1.8 and 6.5 Hz), 5.38 (d, 1H, OH-3'; J=3.3 Hz), 4.73 (t, 1H, OH-5'; J=5.4 Hz), 4.30-4.20 (m, 1H, H-3'), 3.85-3.60 (m, 3H, H-4',5' and 5"), 2.60-2.50 (m, 1H, H-2' partially obscured by DMSO-$d_5$), 1.90 (dd, 1H H-2"; J=1.8 and 14.7 Hz); mass spectra (matrix: glycerol-thioglycerol, 50:50, v/v): FAB>0 339 [M+glycerol+H]$^+$, 247 [M+H]$^+$, 131 [$BH_2$]$^+$ and 115 [s]$^+$; FAB<0 245 [M–H]$^-$ and 129 [B]$^-$.

Anal. Calculated for $C_9H_{11}N_2O_5F$ (M=246.20): C, 43.90; H, 4.51; N, 11.38; F, 7.72. Found: C, 43.60; H, 4.57; N, 11.22; F, 7.40.

1-(5-O-Monomethoxytrityl-2-deoxy-$\beta$-L-threo-pentofuranosyl)-5-fluorouracil (8b)

4-Methoxytriphenylchloromethane (1.96 g; 6.35 mmol) is added to a solution of 7b (1.30 g; 5.28 mmol) in anhydrous pyridine (60 ml). The solution is stirred for 48 h at room temperature and then the solvent is evaporated under reduced pressure. Water and dichloromethane are added. The organic phase is separated, washed successively with a saturated aqueous solution of sodium hydrogen carbonate and water, dried over sodium sulfate and filtered. After evaporation to dryness, the residue is chromatographed on a silica gel column [eluent: step gradient of methanol (0-5%) in dichloromethane] to give 2.6 g (yield 95%) of 8b in foam form: $^1$H NMR (DMSO-$d_6$) $\delta$ ppm: 11.82 (s, 1H, 3-NH), 7.92 (d, 1H, H-6; J=7.3 Hz), 7.5-6.8 (m, 14H, mMTr), 6.11 (d, 1H, H-1'; J=7.9 Hz), 5.35 (d, 1H, OH-3'; J=3.1 Hz), 4.20-4.15 (m, 1H, H-3'), 4.15-4.10 (m, 1H, H-4'), 3.72 (s, 3H, $OCH_3$), 3.40-3.10 (m, 2H, H-5' and 5"), 2.60-2.45 (m, 1H, H-2' partially obscured by DMSO-$d_5$), 1.90 (d, 1H, H-2"; J=14.7 Hz); mass spectrum (matrix: glycerol-thioglycerol, 50:50, (v/v): FAB<0 1553 [3M–H]$^-$, 1035 [2M–H]$^-$, 517 [M–H]$^-$, 245 [M-monomethoxytrityl]$^-$ and 129 [B]$^-$.

5'-O-Monomethoxytrityl-2',3'-dideoxy-$\beta$-L-5-fluorouridin (9b)

This compound is prepared according to a method similar to that used during the synthesis of 9a. Thus, 8b (2.8 g; 5.40 mmol) is reacted with O-phenylchlorothio-formate (1.5 ml; 11.08 mmol) and DMAP (5.97 g, 48.85 mmol) in anhydrous acetonitrile (250 ml) to give, after treatment, a residue which is treated with $Bu_3SnH$ (3.75 ml; 13.93 mmol) and AIBN (0.28 g; 1.70 mmol) in dioxane (95 ml) for 2 h under argon. After treatment, the residue is chromatographed on a silica gel column [eluent: step gradient of methanol (0-2%) in dichloromethane] to give 1.6 g (yield 59% of 9b in foam form: $^1$H NMR (DMSO-$d_6$) $\delta$ ppm: 11.84 (s, 1H, 3-NH), 7.90 (d, 1H, H-6; J=6.8 Hz), 7.50-6.80 (m, 14H, mMTr), 5.95 (d, 1H, H-1'; J=5.9 Hz), 4.20-4.10 (m, 1H, H-4'), 3.72 (s, 3H, $OCH_3$), 3.40-3.15 (m, 2H, H-5' and 5" partially obscured by $H_2O$), 2.40-2.20 (m, 1H, H-2'), 2.20-1.85 (m, 3H, H-2", 3" and 3"'); mass spectrum (matrix: glycerol-thioglycerol, 50:50, v/v); FAB<0 1003 [2M–H]$^-$, 501 [M–H]$^-$, 229 [M-monomethoxytril]$^-$, 129 [B].

2',3'-Dideoxy-$\beta$-L-5-fluorouridine ($\beta$-L-5-FDDU: 10b)

The compound 9b (1.6 g, 3.18 mmol) is dissolved in 80% aqueous acetic acid and the solution is stirred at room temperature for 2 h. After evaporation of the solvents, the residue is coevaporated several times with a toluene-methanol mixture. A silica gel column chromatography [eluent: step gradient of methanol (0-5%) in dichloromethane] gives 0.6 g (yield 82%) of 10b in foam form: $^1$H NMR (DMSO-$d_6$) $\delta$ ppm: 11.76 (s, 1H, 3-NH), 8.38 (d, 1H, H-6; J=7.5 Hz), 5.89 (dd, 1H, H-1'; J=2.0 and 4.0 Hz), 5.20 (t, 1H, OH-5'; J=5.0 Hz); 4.10-4.00 (m, 1H, H-4'), 3.80-3.65 (m, 1H, H-5'; after exchange $D_2O$: 3.69 ppm, dd, J=2.8 and 12.3 Hz), 3.60-3.50 [m, 1H, H-5"; after exchange $D_2O$; 3.50 ppm, dd, J=3.3 and 12.3 Hz], 2.35-2.20 (m, 1H, H-2'), 2.10-1.80 (m, 3H, H-2", 3' and 3"); mass spectra (matrix: glycerol-thioglycerol, 50:50, v/v): FAB>0 231 [M+H]$^+$, 131 [BH2]$^+$, 101 [s]$^+$; FAB<0 229 [M–H]$^-$, [B]$^-$.

EXAMPLE 5

2',3'-Dideoxy-b-L-cytidine ($\beta$-L-DDC, 21a)

Acetic anhydride (0.27 ml; 2.9 mmol) is added at 0° C. to a solution of $\beta$-L-DDU (10a) (0.4 g; 1.88 mmol) in anhydrous pyridin (6 ml) and the reaction mixture is stirred for 1 h at 0° C., and then for 5 h at room temperature. Ice-cold water is then added and the mixture is extracted twice with chloroform. The organic phase is dried over sodium sulfate, filtered, coevaporated several times with toluene and evaporated to dryness to give 0.55 g of a residue corresponding to 5'-O-acetyl-$\beta$-L-DDU (18a) which is sufficiently pure (tlc) to be used directly in the next stage. Lawesson's reagent (Aldrich, Item 22,743-9; 0.64 g; 1.6 mmol) is added to a solution of the residue in anhydrous dichloroethane (49 ml) and the mixture is heated at reflux under argon for 2 h. After evaporation of the solvents, the residue is chromatographed on a silica gel column [eluent: step gradient of methanol (0-1%) in dichloromethane] to give 0.55 g of 5'-O-acetyl-β-L-4-thiouridine (19a) sufficiently pure (tlc) to be used directly in the last step. The residue is dissolved in ammoniacal methanol (11 ml) and the solution is heated at 100° C. for 3 h in an autoclave. The mixture is cooled, evaporated to dryness and the residue is chromatographed on a silica gel column [eluent: step gradient of methanol (0-12%) in dichloromethane] to give 0.33 g (yield 83%) of pure β-L-DDC (21a) which crystallizes from ethanol: m.p.=220-222° C.; UV (EtOH 95) max 273 nm, λmin 252 nm; $^1$H NMR (DMSO-d$_6$) δ ppm=7.89 (d, 1H, H-6; J=7.4 Hz), 7.15-6.95 (broad d, 2H, NH$_2$), 5.91 (dd, 1H, H-1'; J=3.0 and 6.5 Hz), 5.66 (d, 1H, H-5; J=7.4 Hz), 4.99 (t, 1H, OH-5'; J=5.2 Hz), 4.05-3.95 (m, 1H, H-4'), 3.60-3.70 [m, 1H, H-5'; after exchange D$_2$O: dd, 3.64 ppm, J=3.6 and 12.0 Hz], 3.60-3.50 [m, 1H, H-5"; after exchange D$_2$O: dd, 3.50 ppm, J=4.1 and 12.0 Hz], 2.30-2.15 (m, 1H, H-2'), 1.9-1.65 (m, 3H, H-2", 3' and 3"); $[\alpha]_D^{20}$ −103.6 (c, 0.8, methanol); mass spectra (matrix: glycerol-thioglycerol, 50:50, v/v): FAB>0 423 [2M+H]$^+$, 304 [M+glycerol+H]$^+$, 212 [M+H]$^+$, 112 [BH$_2$]$^+$, 101 [s]$^+$; FAB<0 210 [M−H]$^−$.

Anal. Calculated for C$_9$H$_{13}$N$_3$O$_3$ (M=211.21): C, 51.18; H, 6.20; N, 19.89. Found: C, 51.34; H, 6.25; N, 20.12.

EXAMPLE 6

2',3'-Dideoxy-β-L-5-fluorocytidine (β-L-5-FDDC, 21b)

Acetic anhydride (0.34 ml; 3.60 mmol) is added at 0° C. to a solution of β-L-5-FDDU (10b) (0.55 g; 2.39 mmol) in anhydrous pyridine (10 ml) and the reaction mixture is stirred for 1 h at 0° C. and then for 3 h at room temperature. An additional quantity of acetic anhydride (0.22 ml; 2.33 mmol) is added and the stirring is continued for 3 h at room temperature. Ice-cold water is then added and the mixture is extracted twice with chloroform. The organic phase is dried over sodium sulfate, filtered, coevaporated several times with toluene, and evaporated to dryness to give 0.67 g of a residue corresponding to 5'-O-acetyl-β-L-5-FDDU (18b) sufficiently pure (tlc) to be used directly in the next step. Lawesson's reagent (0.60 g; 1.48 mmol) is added to a solution of the residue in anhydrous dichloroethane (67 ml) and the mixture is heated at reflux under argon. Two additional quantities of Lawesson's reagent are added, after 2 h (0.41 g; 1.01 mmol) and 3 h (0.20 g; 0.49 mmol) of reflux respectively. After evaporation of the solvents, the residue is chromatographed on a silica gel column [eluent: step gradient of methanol (0-2%) in dichloromethane] to give 0.48 g of 5'-O-acetyl-β-L-5-fluoro-4-thiouridine (19b) sufficiently pure (tlc) to be used directly in the last step. The residue is dissolved in ammoniacal methanol (12 ml) and the solution is heated at 100° C. for 3 h 30 min in an autoclave. The mixture is cooled, evaporated to dryness and the residue is chromatographed on a silica gel column [eluent: step gradient of methanol (0-8%) in dichloromethane] to give 0.27 g (yield 51%) of pure β-L-5-FDDC (21b) which crystallizes from ethyl acetate: m.p.=158-160° C.; UV (EtOH 95) λmax 281 nm (ε, 8400) and 237 nm (ε, 8500); min 260 nm (ε, 5700) and 225 nm (ε, 7800); $^1$H NMR (DMSO-d$_6$) δ ppm 8.28 (d, 1H, H-6; J=7.4 Hz), 7.7-7.4 (broad d, 2H, NH$_2$), 5.83 (poorly resolved dd, 1H, H-1'), 5.16 (t, 1H, OH-5'; J=5.1 Hz), 4.05-3.95 (m, 1H, H-4'), 3.8-3.70 [m, 1H, H-5'; after exchange D$_2$O: dd, 3.71 ppm, J=2.7 and 12.3 Hz], 3.60-3.50 [m, 1H, H-5"; after exchange D$_2$O: dd, 3.52 ppm; J=3.3 and 12.3 Hz], 2.35-2.15 (m, 1H, H-2'), 1.95-1.75 (m, 3H, H-2", 3' and 3"); $[\alpha]_D^{20}$ −80.0 (−c 1.0, DMSO); mass spectra (matrix: 3-nitrobenzyl alcohol FAB>0 230 [M+H]$^+$; 130 [BH$_2$]$^+$ and 101 [s]$^+$; FAB<0 228 [M−H]$^−$.

Anal. Calculated for C$_9$H$_{12}$N$_3$FO$_3$ (M=229.21): C, 47.16; H, 5.28; N, 18.33; F, 8.29. Found: C, 46.90; H, 5.28; N, 18.07; F, 8.17.

The compounds of the invention were subjected to pharmacological tests which show their benefit in the treatment of viral diseases.

Evaluation of the Anti-HIV 1 Activity on Various Cell Lines.

HIV=human immunodeficiency virus.

The replication of HIV-1 (LAI isolate) in cell lines is measured by a reverse transcriptase (RTase) assay in the culture supernatant after 5 days of infection. This activity indicates the presence of a virus liberated by the cells. After adsorption of the virus, the test compounds are added at various concentrations to the culture medium.

The antiviral activity is expressed by the lowest concentration of compound which reduces the production of RTase by at least 50% (ED$_{50}$).

The toxic effect on the noninfected cells is assessed by calorimetric reaction based on the capacity of live cells to reduce 3-(4,5-dimethylthiozol-2-yl)-2,5-diphenyltetrazolium bromide to formazan after incubating for 5 days in the presence of various concentrations of the compounds. The results are expressed as the lowest concentration of compound which causes at least 50% inhibition of the formation of formazan (CD$_{50}$).

β-L-DDC (21a) and even more so β-L-5FDDC (21b) have a marked ED$_{50}$ on HIV-1 and HIV-2 as indicated below.

| Composés: | | 21a | 21b | AZT | DDC |
|---|---|---|---|---|---|
| CEM-SS/HIV-1 LAI | ED$_{50}$ | $3 \times 10^{-7}$ M | $3.8 \times 10^{-8}$ M | $2.5 \times 10^{-9}$ M | $3.5 \times 10^{-8}$ M |
| | CD$_{50}$ | $8.3 \times 10^{-5}$ M | $9 \times 10^{-5}$ M | $>10^{-4}$ M | $6 \times 10^{-5}$ M |
| PBM/HIV 1 III B | ED$_{50}$ | $3.5 \times 10^{-7}$ M | $3 \times 10^{-8}$ M | $1.1 \times 10^{-9}$ M | $4 \times 10^{-8}$ M |
| | CD$_{50}$ | $10^{-4}$ M | $10^{-4}$ M | $7 \times 10^{-5}$ M | $7 \times 10^{-5}$ M |
| PBMC/HIV-2 D 194 | ED$_{50}$ | $3.5 \times 10^{-8}$ M | $4.5 \times 10^{-8}$ M | $1 \times 10^{-9}$ M | $2 \times 10^{-9}$ M |
| | CD$_{50}$ | $10^{-4}$ M | $10^{-4}$ M | $8 \times 10^{-5}$ M | $2.5 \times 10^{-5}$ M |

Furthermore, this anti HIV-1 activity is confirmed on various other cell lines:

MT-4 (ED$_{50}$: 21a $1.5 \times 10^{-5}$ M, 21b $2.4 \times 10^{-6}$ M; Ref: AZT $2.7 \times 10^{-8}$ M, DDC $2.5 \times 10^{-6}$ M)

U 937 (ED$_{50}$: 21a $1.5 \times 10^{-7}$ M, 21b $4.2 \times 10^{-10}$ M; Ref: AZT $4 \times 10^{-10}$ M, DDC $3.8 \times 10^{-10}$ M)

CEM TX$^-$ (ED$_{50}$: 21a $9.5 \times 10^{-8}$ M, 21b $9.5 \times 10^{-8}$ M; Ref: AZT>$10^{-4}$ M, DDC $2.5 \times 10^{-6}$ M)

Finally, these compounds also exhibit an anti-HIV-1 activity on the lines resistant to AZT and Nevirapine CEM-SS/HIV-1 Nevirapine resistant ($ED_{50}$: 21a $10^{-6}$ M, 21b $7.2 \times 10^{-7}$ M; Ref: AZT $7.5 \times 10^{-6}$ M, DDC $1.2 \times 10^{-7}$ M)

MT2/HIV-1 AZT resistant (Larder) ($ED_{50}$: 21a $3.5 \times 10^{-7}$ M, 21b $2 \times 10^{-7}$ M; Ref: AZT $7 \times 10^{-6}$ M, DDC $2.2 \times 10^{-7}$ M)

Legend to FIG. 1

Scheme I: Bases=purines or pyrimidines, optionally appropriately protected; R=Benzoyl (Bz), acetyl (Ac), monomethoxytrityl (mMTr), or tert-butyldiphenylsilyl

The invention claimed is:

1. A method for the preparation of 2'- or 3'-deoxy- and 2',3'-dideoxy-β-L-pentofuranonucleoside compounds of formula I:

(I)

in which

B represents purine or pyrimidine base selected from the group consisting of adeninyl, guaninyl, hypoxanthinyl, uracilyl, thyminyl, cytosinyl, 5-halo-uracilyl and 5-halo-cytosinyl;

$R_1$ represents OH;

$R_2$ and $R_3$ represent, independently of each other, H or OH; and at least one of $R_2$ and $R_3$ represents H;

comprising the following steps:

1) a compound of formula (II) is condensed with the base B' with an appropriate coupling reagent in order to obtain the compound of formula (III) according to the scheme wherein:

$R'_1$ and $R'_2$ have the meanings given for $R_1$ and $R_2$ except that when $R_1$ and $R_2$ represent OH, the OH group is protected by a protecting group selected from the group consisting of an acyl, a benzoyl, a benzyl and a silyl group, $R'_3$ is a $C_1$ to $C_5$ alkyl group or a phenyl radical, X is a leaving group selected from Cl, Br, I, a $C_1$ to $C_5$ acyloxy and $C_1$ to $C_5$ alkoxy group, B' is a purine or pyrimidine base B which is protected by an amino protecting group selected from the group consisting of an acyl, a benzoyl, a benzyl and a silyl group when necessary, 2) the $R'_3COO$ group at the 2' position is removed by deacetylation so as to obtain an OH group and a compound of formula (IV)

3) optionally, the OH group at the 2' position is removed by a deoxygenation reaction; and 4) where appropriate, the $R'_1$ and $R'_2$ groups and the B' base are deprotected so as to obtain the compounds of formula (I).

2. The method according to claim 1, wherein $R'_3$ is a $C_1$ to $C_5$ alkyl group.

3. The method according to claims 1 or 2, further comprising preparing the compound (II), in which X and $R'_3COO$ represent an O-acetyl group, by acetolysis of a 1,2-isopropylidenyl-L-xylofuranose compound of formula (V)

(V)

4. The method according to claim 1, wherein $R'_2$ and $R'_3COO$ are different.

5. The method according to claim 1, wherein the B is selected from the group consisting of adeninyl, guaninyl, hypoxanthinyl, uracilyl, thyminyl, cytosinyl, 5-halo-uracilyl and 5-halo-cytosinyl.

6. The method according to claim 1 for the preparation of a compound of formula (I) in which B is cytosinyl, further comprising a step wherein a compound in which B is uracilyl is converted to a compound of Formula I in which B is cytosine by converting uracilyl to cytosinyl by the process of:

i) adding acetic anhydride and pyridine;
ii) adding Lawesson's reagent and dichloroethane; and
iii) adding ammonical methanol.

7. A stereoisomeric β-L-pentofuranonucleoside compound corresponding to the following formula (I)

in which

B selected from the group consisting of adeninyl, guaninyl, hypoxanthinyl, uracilyl, thyminyl, cytosinyl, 5-halo-uracilyl and 5-halo-cytosinyl;

$R_1$ represents OH and, either $R_2$ represents OH and $R_3$ represents H, or $R_2$ represents H and $R_3$ represents OH.

8. The compound according to claim 7, wherein B represents uracilyl, cytosinyl or 5-fluorocytosinyl.

9. The method according to claim 1, wherein $R'_3$ represents $CH_3$.

10. The coupling reagent present in the condensing step of claim 1 is selected from the group consisting of tin (IV) chloride, a mixture of hexamethyldisilazane and chlorotrimethylsilane, a mixture of N, O-bis(trimethylsilyl)acetamide and trimethylsilyl triflate, and a mixture of hexamethyldisilazane and trimethylsilyl triflate.

* * * * *